(12) United States Patent
Patangay et al.

(10) Patent No.: US 9,597,029 B2
(45) Date of Patent: Mar. 21, 2017

(54) SYSTEM AND METHOD FOR REMOTELY EVALUATING PATIENT COMPLIANCE STATUS

(75) Inventors: Abhilash Patangay, St. Paul, MN (US); Shelley Marie Cazares, Washington, DC (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2245 days.

(21) Appl. No.: 11/820,798

(22) Filed: Jun. 19, 2007

(65) Prior Publication Data

US 2008/0319272 A1 Dec. 25, 2008

(51) Int. Cl.
| | |
|---|---|
| *A61B 5/00* | (2006.01) |
| *G06F 19/00* | (2011.01) |
| *A61N 1/00* | (2006.01) |
| *A61B 5/16* | (2006.01) |
| *A61N 1/372* | (2006.01) |

(52) U.S. Cl.
CPC .............. *A61B 5/16* (2013.01); *A61B 5/0002* (2013.01); *A61B 5/165* (2013.01); *A61B 5/4833* (2013.01); *A61B 5/686* (2013.01); *A61B 5/74* (2013.01); *A61N 1/372* (2013.01); *G06F 19/34* (2013.01); *G06F 19/3418* (2013.01); *G06F 19/3475* (2013.01)

(58) Field of Classification Search
None
See application file for complete search history.

(56) References Cited

U.S. PATENT DOCUMENTS

| | | | |
|---|---|---|---|
| 6,024,699 A | 2/2000 | Surwit et al. | |
| 6,083,248 A | 7/2000 | Thompson | |
| 6,168,563 B1 | 1/2001 | Brown | |
| 6,171,256 B1 | 1/2001 | Joo et al. | |
| 6,263,245 B1 | 7/2001 | Snell | |
| 6,416,471 B1 | 7/2002 | Kumar et al. | |
| 6,827,670 B1 | 12/2004 | Stark et al. | |
| 7,468,032 B2* | 12/2008 | Stahmann et al. | 600/301 |
| 7,765,113 B2* | 7/2010 | Ware et al. | 705/3 |
| 2002/0019747 A1* | 2/2002 | Ware et al. | 705/2 |
| 2002/0198473 A1* | 12/2002 | Kumar et al. | 600/595 |
| 2003/0036685 A1* | 2/2003 | Goodman | 600/300 |
| 2004/0122297 A1* | 6/2004 | Stahmann et al. | 600/300 |

(Continued)

OTHER PUBLICATIONS

Health Insurance Portability and Accountability Act of 1996, Pub. L. No. 104-191, 110 Stat. 1936 (Aug. 21, 1996).

(Continued)

*Primary Examiner* — William Thomson
*Assistant Examiner* — Marie Archer
(74) *Attorney, Agent, or Firm* — Pauly, DeVries Smith & Deffner, LLC (57) ABSTRACT

A system and method for remotely evaluating patient compliance status is presented. Compliance to a course of treatment is periodically checked through qualitative inquiry of a patient under remote management. Physiometry of the patient, that indicates emotional state, is remotely monitored contemporaneously with the qualitative state. Patient status is evaluated, including at least one of corroborating the compliance and identifying an emotional imbalance, based upon the indicated emotional state of the patient.

26 Claims, 5 Drawing Sheets

(56) References Cited

U.S. PATENT DOCUMENTS

| | | | |
|---|---|---|---|
| 2004/0181145 A1* | 9/2004 | Al Bandar | A61B 5/164 600/408 |
| 2005/0113652 A1* | 5/2005 | Stark et al. | 600/300 |
| 2006/0064030 A1* | 3/2006 | Cosentino | A61B 5/0031 600/547 |
| 2006/0200007 A1* | 9/2006 | Brockway | A61B 5/00 600/300 |
| 2006/0224419 A1* | 10/2006 | Servizio et al. | 705/2 |
| 2007/0021979 A1* | 1/2007 | Cosentino et al. | 705/2 |
| 2007/0033072 A1* | 2/2007 | Bildirici | 705/3 |
| 2007/0100216 A1* | 5/2007 | Radcliffe et al. | 600/300 |
| 2007/0106127 A1* | 5/2007 | Alman | 600/300 |
| 2007/0179349 A1* | 8/2007 | Hoyme et al. | 600/300 |
| 2007/0179361 A1* | 8/2007 | Brown et al. | 600/300 |
| 2007/0185391 A1* | 8/2007 | Morgan | 600/301 |
| 2008/0001735 A1* | 1/2008 | Tran | 340/539.22 |
| 2008/0004904 A1* | 1/2008 | Tran | 705/2 |
| 2008/0032267 A1* | 2/2008 | Suzansky | 434/1 |
| 2008/0146888 A1* | 6/2008 | Azzaro et al. | 600/300 |
| 2008/0161661 A1* | 7/2008 | Gizewski | 600/306 |
| 2008/0214903 A1* | 9/2008 | Orbach | 600/301 |

OTHER PUBLICATIONS

E. Hammond, "National Committee on Vital and Health Statistics, Subcommittee on Health Data Needs, Standards and Security," http://www.ncvhs.hhs.gov/970211t3.htm, pp. 1-4 (Feb. 11, 1997).

Security and Electronics Signature Standards; Proposed Rule, Federal Register, vol. 63, No. 155 (Aug. 12, 1998).

A. Michalsen et al., "Preventable Causative Factors Leading to Hospital Admission With Decompensated Heart Failure," 80 Heart, pp. 437-441 (1998).

S.J. Bennett et al., "Characterization of the Precipitants of Hospitalization for Heart Failure Decompensation," 7 Am. J. of Crit. Care 3, pp. 168-174 (May 1998).

M.H.L. Van Der Wal et al., "Compliance in Heart Failure Patients: The Importance Of Knowledge And Beliefs," 27 Euro. Heart J., pp. 434-440 (2006).

K. Bonsor, "How Lie Detectors Work," http://people.howstuffworks.com/lie-detector.htm, (Jul. 17, 2001).

R.T. Tsuyuki, "Acute Precipitants of Congestive Heart Failure Exacerbations," 161 Archives of Internal Med., pp. 2337-2342 (Oct. 22, 2001).

* cited by examiner

SYSTEM AND METHOD FOR REMOTELY EVALUATING PATIENT COMPLIANCE STATUS

FIELD

The invention relates in general to remote patient management and, specifically, to a system and method for remotely evaluating patient compliance status.

BACKGROUND

Effectively managing patients with chronic disorders requires balancing their treatment with the compensatory mechanisms of the body. A deviation from a prescribed course of treatment, such as continuing to smoke or drink alcohol when instructed otherwise by a caregiver, could result in a downward health trend. Non-compliance with medication or dietary restrictions is the leading preventable cause of acute coronary decompensation. A. Michalsen et al., *Preventable Causative Factors Leading To Hospital Admission With Decompensated Heart Failure*, 80 HEART 437-441 (1998), and S. J. Bennett et al., *Characterization of the Precipitants of Hospitalization for Heart Failure Decompensation*, 7 AM. J. OF CRIT. CARE 3:168-174 (May 1998), the disclosures of which are incorporated by reference. Consequently, patient management requires continually evaluating both clinical trajectory and patient compliance.

Caregivers play an active role in patient management by periodically seeing patients in-clinic for diagnosis and follow-up. When intervention is required, caregivers generally will prescribe a course of treatment that can include medication, dietary restrictions, lifestyle changes, and other directions, such as described in M. H. L. van der Wall et al., *Compliance And Heart Failure Patients: The Importance Of Knowledge And Beliefs*, 27 EURO. HEART J. 434-440 (2006), the disclosure of which is incorporated by reference. Additionally, as an aid in managing patients, caregivers are increasingly relying upon physiometry obtained through remote monitoring, particularly when in-clinic follow-up is infrequent or impracticable. For example, patient-operable interrogators, commonly known as "repeaters" or "communicators," enable caregivers to remotely gather hemodynamic data and general patient physiometry for managing CHF. Changes in patient condition detected through monitoring that might indicate a need for further intervention are thereby identified sooner than would otherwise be possible, absent remote patient management.

Nevertheless, managing a chronic disorder through remote at-home monitoring lacks the interpersonal dynamic of an in-clinic visit. The patient uses a remote communicator that periodically interrogates any implantable or external medical devices. Recorded data is thereafter uploaded for caregiver review and evaluation. Qualitative "soft" data can be collected through the communicator or other device through interactive questioning regarding a patient's perceived health and well-being. Although questions can be tailored to a particular patient's circumstances, the inquiry remains divorced from factors indicating possible patient non-compliance or emotional imbalance, such as abnormal physiometry.

U.S. Pat. No. 6,168,563, to Brown, discloses a system and method that enables a healthcare provider to monitor and manage a health condition. A clearinghouse computer communicates with a patient through a data management unit that monitors the patient's health. Physiological monitoring devices, such as a blood glucose monitor or peak-flow meter, may also supply patient information. Healthcare professionals can access the patient information through the clearinghouse computer, which can process, analyze, print, and display the data. Although the patient queries can address specific healthcare concerns, Brown fails to corroborate the monitored information with patient compliance.

U.S. Pat. No. 6,263,245 issued Jul. 17, 2001, to Snell, describes a portable system and method for conducting wireless interrogation of an implantable medical device (IMD). A portable interrogation device can be directly interfaced with a data processing device, such as a programmer/analyzer. The device includes a control circuit for controlling transmission, a transmitter, a receiver for receiving IMD interrogation signals, memory for storing data, and an electronic communications interface for delivering to the data processing device. However, the device only facilitates relay of data without analysis or processing and fails to corroborate the interrogated data with patient compliance.

Therefore, there is a need for an approach to tying the remote monitoring of patients, particularly those patients who are suffering from a chronic disorder, to patient compliance to a prescribed course of treatment and recognition of potential emotional imbalance. Preferably, such an approach would link the emotional state observed to physiometry measured at about the same time.

SUMMARY

A system and method for remote patient compliance checking includes an assessment of both qualitative, that is, subjective "soft" patient responses and quantitative, that is, objective "hard" physiometry, which are both recorded contemporaneous to application of a patient compliance questionnaire or inquiry. Patient physiometry is remotely monitored during interactive compliance checks to corroborate compliance and to identify possible emotional imbalance or other indications that may require further patient inquiry. The physiometry can be evaluated against different compliance criteria, including absolute thresholds, overall trends, or relative baselines to identify departures from normative or expected values. Based upon the patient's responses, the compliance checking may be modified dynamically to inquire in further depth as to those compliance or emotional stability areas where the respective perceived compliance or emotional states of the patient are not as expected.

One embodiment provides a system and method for remotely evaluating patient compliance status. Compliance to a course of treatment is periodically checked through qualitative inquiry of a patient under remote management. Physiometry of the patient, that indicates emotional state, is remotely monitored contemporaneously with the qualitative state. Patient status is evaluated, including at least one of corroborating the compliance and identifying an emotional imbalance, based upon the indicated emotional state of the patient.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Although described in this application in relation to medical devices primarily intended for providing cardio and cardiopulmonary diagnosis, therapy, monitoring, the embodiments described apply generally to all forms of medical devices capable of being remotely interrogated or programmed, whether implantable or external.

System

Figure 1:
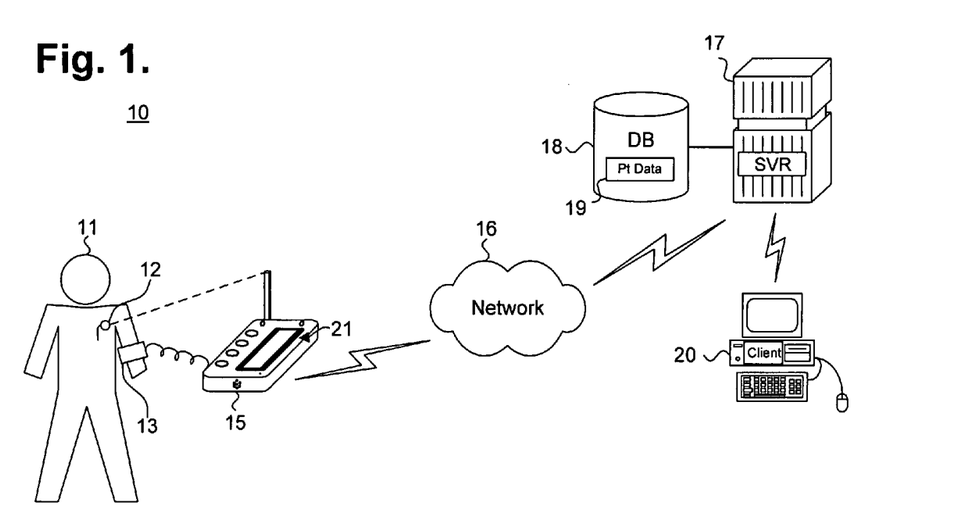
FIG. 1 is a functional block diagram showing a system for remotely evaluating patient compliance status, in accordance with one embodiment.

Ensuring patient compliance to a prescribed course of treatment and emotional balance are crucial for all patients, particularly when remotely managed. FIG. 1 is a functional block diagram showing a system 10 for remotely evaluating patient compliance status, in accordance with one embodiment. Evaluating whether patients are in compliance and emotionally stable is necessary for recipients of implantable medical devices (IMDs), as well as for patients who are under monitoring through other means, such as by external medical devices, whether permanent or for the purposes of ensuring compliance.

At a minimum, evaluating patient compliance status to a prescribed course of treatment and emotional stability requires an ability to remotely determine the perceived emotional state of a patient 11 as an indication of whether the patient 11 is in compliance. However, assessing emotional state can be subjective and the remote displacement of the patient 11 away from a clinic environment prevents a caregiver from physically observing and evaluating the patient in-person. As a result, patient physiometry must be used as a surrogate for an in-person caregiver assessment. The physiometry is obtained during remote questioning on compliance or other matters and can be sensed, monitored, and recorded by an IMD 12, external medical device (EMD) 13, or combination of devices, which function independently from or in conjunction with a communicator 15 or other patient-operable device.

Figure 2:
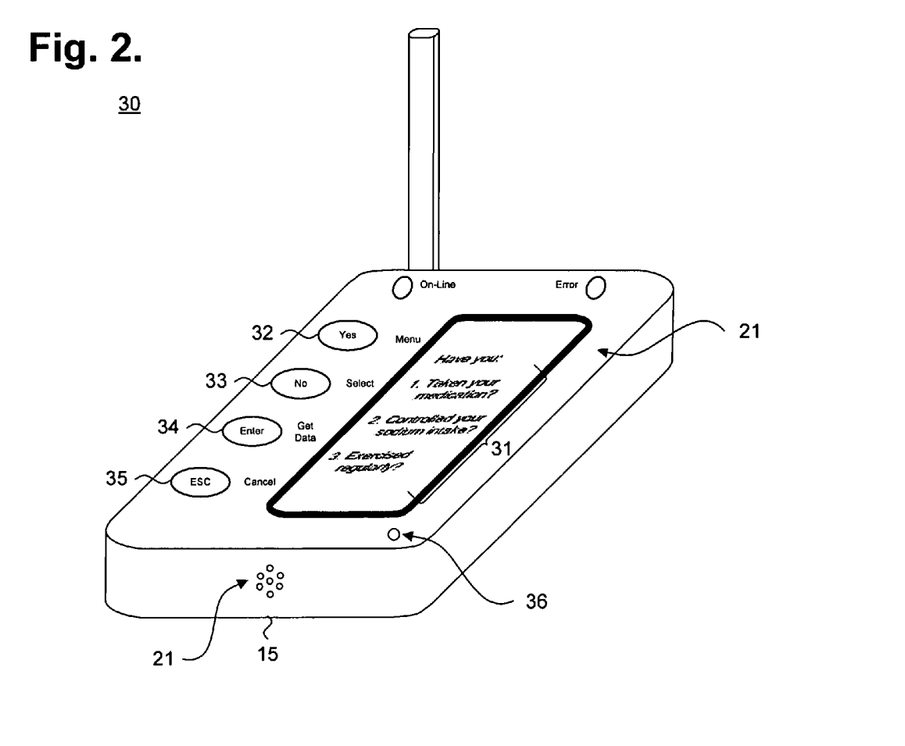
FIG. 2 is a block diagram showing a communicator for use with the system of FIG. 1.

By way of example, the patient 11 is coupled to a communicator 15, which both provides an interactive inquiry regarding patient compliance and emotional state over a user interface 21 and monitors the patient's physiometry contemporaneous to the inquiry, as further described below with reference to FIG. 2. The external sensors, which are integral or connected to an EMD 13, are interfaced to the communicator 15 by wired or wireless means, such as inductive or radio frequency telemetry or other forms of wireless telemetry based on, for example, "strong" Bluetooth or IEEE 802.11 interfacing standards. Other types of devices for interfaces are possible. The external sensors are provided either for purposes of medical care or for the express purpose of obtaining physiometry during patient compliance evaluation. The external sensors can include sensors that remain in contact with the patient's body, such as a Holter monitor, as well as a wide range of medical and non-medical devices that a patient can use, operate, or upon which he can perform testing, such as a blood pressure cuff, weight scale, Spiro meter, skin resistance sensor, and the like. Internal sensors can similarly be provided integral or connected to an IMD 12. Other types of devices for physiometric data collection are possible.

In a further embodiment, patient data monitoring is also recorded, collected, and analyzed on a regular and continuous basis by implantable or external medical devices. Patient monitoring data is broadly defined. Patient data includes quantitative physiometric data that has been recorded or derived from raw physiometry measured by a medical device. Patient data also includes non-patient information, such as parametric data reporting on the status and operational characteristics of the medical device itself, and environmental data that includes non-medical device related information, such as the ambient temperature or time of day. Patient data can also include qualitative data values, such as subjective impressions of personal wellness or quality of life. Still further types of patient data are possible.

Patient data can originate with one or more IMDs 12 that are permanently or temporarily introduced into a patient's body. These devices include IMDs 12 that are totally introduced into a patient's body, which include therapy delivery devices, such as pacemakers, implantable cardiac defibrillators, drug pumps, and neuro-stimulators; and physiometric monitoring devices, such as cardio or and pulmonary monitors. These devices also include IMDs 12 that are partially introduced into a patient's body, which include therapy delivery devices, such as remotely controlled insulin pumps consisting of an extracorporeal controller and an implanted bolus delivery device, and physiometric monitoring devices, such as electroencephalogram recorders consisting of an extracorporeal recording device electrodes that are placed subdurally or in the cerebral cortex. Other types of IMDs are possible.

Generally, those IMDs 12 that are either permanently introduced, or which are totally implanted require extracorporeal interfacing to interrogate or retrieve patient data and to provide programming over the operation of the IMD 12 while in situ. Extracorporeal interfacing to these types of IMDs 12 can be provided through conventional interrogation devices, such as programmers (not shown), communicators 15, or similar devices, which are interfaced to an IMD through wired or wireless means, such as inductive radio frequency telemetry, or other forms of wireless telemetry based on, for example, "strong" Bluetooth or IEEE 802.11 interfacing standards. Other types of devices interfaces are possible.

In a further embodiment, extracorporeal interfacing can be provided through a server 17, which is remotely interfaced over a network 16, either directly with an AIMD or via an intermediary interface. Structurally, the server 17 is a server-grade computing platform configured as a uni-, multi- or distributed processing system, which includes those components conventionally found in computing devices, such as, for example, a central processing unit (CPU), memory, network interface, persistent storage, and various components for interconnecting such components. The server 17 can include a database 18 or other storage means to maintain retrieved patient data 19 and other information for caregiver review and analysis, and other authorized uses. The network 16 is based on the Transmission Control Protocol/Internet Protocol (TCP/IP) protocol suite, although other protocol suites are possible. Additionally, other network topologies and configurations are possible.

In a further embodiment, the patient data can be evaluated for the occurrence of one or more chronic or acute health conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 4, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a still further embodiment, the patient data is extracorporeally safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Communicator

A communicator is one form of patient-operable device suitable for obtaining physiometry while concurrently checking patient compliance. FIG. 2 is a block diagram showing a communicator 15 for use with the system 10 of FIG. 1. The communicator 15 is configured for patient operation in an at-home, non-clinical setting and can automatically report patient compliance results to a centralized repository, such as a server 17 (shown in FIG. 1) or other caregiver-accessible facility. Other types of patient-operable devices with comparable physiometric data collection and user interfacing capabilities could also be used, as further described below with reference to FIG. 9.

In general, communicators are devices used to interrogate patients' medical devices 12, particularly IMDs accessible through wireless telemetry. Thus, the communicator 15 primarily functions as a medical device interrogation interface. During each interrogation session, the communicator 15 collects stored physiometric monitoring data and other information for evaluation, relay, and storage. Interrogation sessions preferably occur on a regular basis.

When properly equipped, a communicator 15 can also function as a patient compliance checking device, which requires an interactive user interface 21 and an ability to collect physiometric data from the patient contemporaneous to compliance questioning. The user interface 21 receives user inputs and provides automated outputs. User inputs can be received through a plurality of buttons 32-35, including a keypad; via a touch-sensitive screen (not shown); with a mouse or trackball (not shown); or by other user manipulable device. Automated outputs can be provided via visual display 31 for presenting a compliance questionnaire or other information to the patient 11, or by other user perceivable device. In a further embodiment, the user interface 21 is implemented as an interactive voice response system, which respectively includes a microphone 36 for user inputs and speaker 37 for providing automated outputs. Other forms of user interface implementations, features, and functions are possible.

The contemporaneous collection of physiometric data can be provided by either the device itself or through external sensors, which can be wearable by the patient, placed proximate to the patient, or permanently affixed to the patient's body. In a further embodiment, the physiometric data can be collected by the patient's medical devices 12, either in conjunction with or in lieu of the sensors 13. In a still further embodiment, the patient medical devices 12 can be used as the exclusive source of the physiometry, in situations in which the sensors 13 are unavailable or the communicator 15 lacks a separate interface to external sensors. Other approaches to interfacing sensors and of contemporaneously obtaining physiometric data from the patient are possible.

To assess the patient's compliance, the communicator 15 queries that patient 11 using a compliance questionnaire via the user interface 21 while contemporaneously measure the patient's physiometric data. However, other forms of obtaining compliance responses are possible, such as visual analog scales; five factor wellness scales (creative, coping, physical, essential, social); comfort, pain, stress, or spiritual wellness scales; spoken or written wellness journals; and present-time or time-to-time day logs. Still further forms of subjective compliance checking are possible.

Patient Compliance

Figure 3:
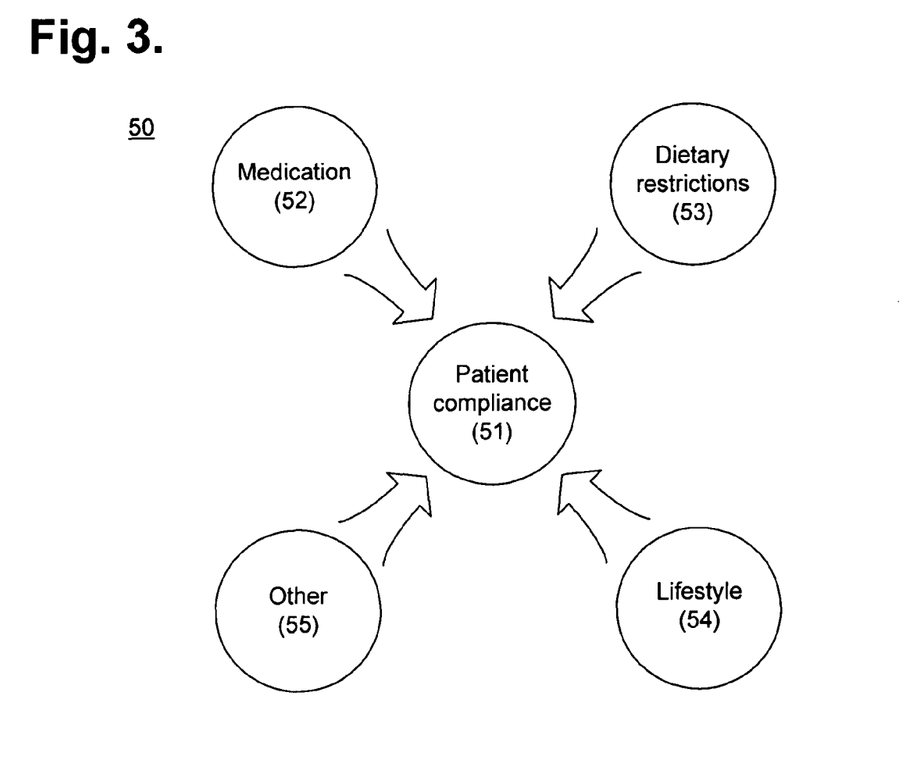
FIG. 3 is a data flow diagram showing, by way of example, factors bearing on patient compliance to a course of treatment.

In simplest form, patient compliance refers to adherence by a patient to a medical regimen, which is generally prescribed by a caregiver as a course of treatment for a chronic disorder. Ensuring compliance, as well as emotional stability, are crucial parts of effective patient management. Patient compliance itself is multi-faceted. FIG. 3 is a data flow diagram showing, by way of example, factors 50 bearing on patient compliance 51 to a course of treatment. The factors include medication or prescribed drugs 52; dietary restrictions 53, such as limits on daily fluid intake or restrictions on sodium; and lifestyle modifications 54, such as refraining from smoking or drinking alcohol, or undertaking light daily exercise. Other factors 55 relating to compliance 51 are possible and no single factor is dispositive of whether a patient is in compliance. The amount of weight assigned to each factor can depend upon the underlying disorder, caregiver preference, clinical trajectory, and patient profile, such as sex, age, smoking habits, number and dates of previous hospital admissions, prescribed drugs, and dietary treatment. Other considerations on the relative importance of each factor are possible.

Emotional Stability

Figure 4:
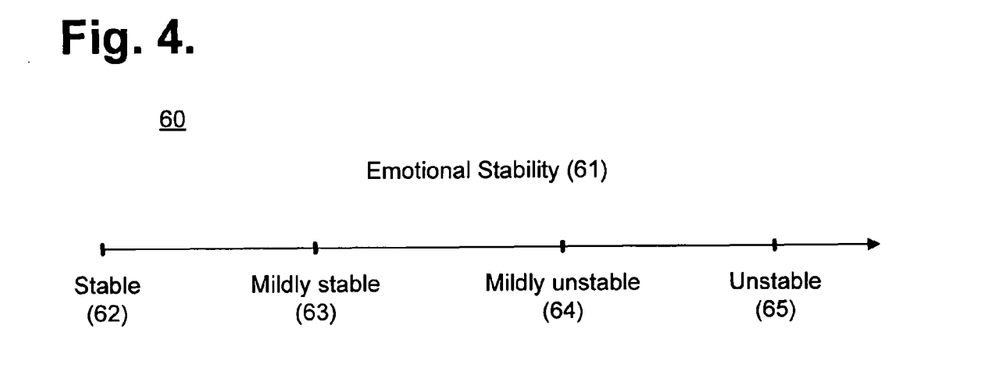
FIG. 4 is a data flow diagram showing, by way of example, levels of patient emotional stability.

The mental well being can also influence patient compliance. Mental imbalance, whether transient or long term, can present through both quantitative data, such as serotonin, and qualitative indicators, such as emotional response. FIG. 4 is a data flow diagram showing, by way of example, levels 60 of patient emotional stability 61. The overall emotional stability 61 of the patient can be measured using a relative scale, such as along a continuum or set of discrete emotional states, such as stable 62, mildly stable 63, mildly unstable 64, and unstable 65. The relative level can be based on the physiometry or compliance questionnaire responses and can be determined from session to session, by sampling or average, or through other evaluative means. Additionally, other emotional states are possible.

Method

Figure 5:
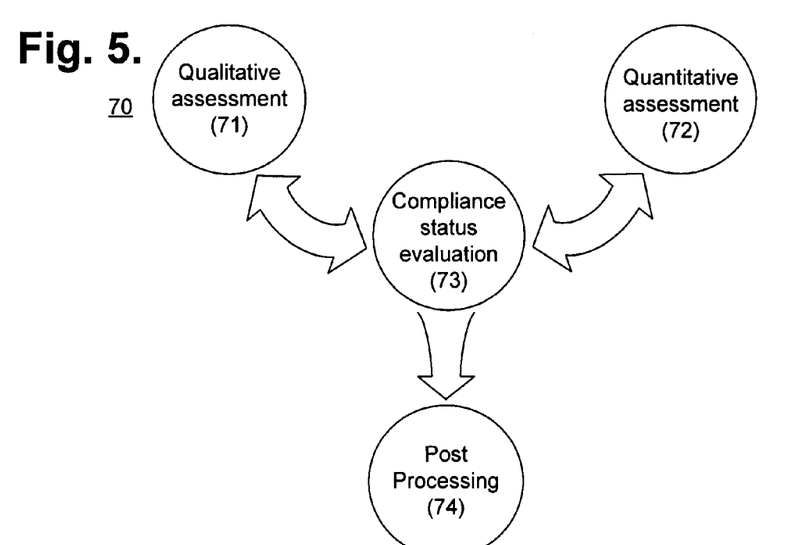
FIG. 5 is a process flow diagram showing a method for remotely evaluating patient compliance status, in accordance with one embodiment.

Patient compliance is remotely evaluated by simultaneously assessing a patient's subjective responses and measured objective physiometry. The pairing of the quantitative "hard" physiometry to the qualitative "soft" patient responses provides insight into the patient's emotional state as pertaining to adherence to the prescribed course of treatment. FIG. 5 is a process flow diagram showing a method 60 for remotely evaluating patient compliance status, in accordance with one embodiment. The method is performed as a series of process steps by a communicator 15, or general purpose programmable computing device, such as a personal computer, cellular telephone, or other network-capable device.

Determining compliance requires cooperation and candor by the patient. Evaluation of patient compliance is performed preferably on a regular basis or as necessary. The most direct approach to checking compliance is through questions and answers regarding the compliance factors. Patient compliance answers are assessed contemporaneously with and are corroborated against physiometric data. Thus, qualitative assessment (operation 71) and quantitative assessment (operation 72) occur at the same time. Initially, the form of questioning during qualitative assessment (operation 71) proceeds in summary fashion with equal emphasis being placed on the compliance factors as appropriate.

Questionnaires regarding compliance can be tailored to the needs and abilities of each patient. At one extreme, questionnaires can be strictly formatted using direct inquiries, such as by using a question-and-answer format. At the other extreme, the questionnaires can be spoken or loosely formatted, such as written or spoken wellness journals or present-time- or time-to-time day logs. In between the two extremes, the questionnaires can utilize relative inquiries, such as visual analog scales; five factor wellness scales, for instance, creative, coping, physical, essential, social; comfort scales; pain scales; stress scales; or spiritual wellness scales. Other forms of questionnaires for obtaining subjective answers regarding compliance are possible.

The compliance responses and physiometry obtained are evaluated to determine the compliance status of the patient, which can include corroborating compliance to a course of treatment, identifying any apparent emotional imbalance, or both (operation 73). The evaluation can occur following each response, at the end of a series or section of questions pertained to a specific compliance factor, or upon the close of the session. The evaluation establishes the patient's perceived emotional state, as further described below with reference to FIG. 6. The emotional state can then be applied to other facets of care giving through post processing (operation 74), as further described below with reference to FIG. 7.

The nature, ordering, and directness of the compliance questioning can be modified dynamically during compliance status evaluation (operation 73) to explore individual factors in greater depth, such as when the patient's physiometry during quantitative assessment (operation 72) indicates an emotional state perceived as a departure from normative or expected values. For instance, the detection of an increased heart rate or decreased level of skin resistance during questioning concerning a patient's smoking habits may indicate possible non-compliance and would warrant further inquiry as to lifestyle factors. The normative emotional state for a patient can be established through different compliance criteria, including absolute thresholds, overall trends, or relative baselines, as further described below with reference to FIG. 8.

Emotional State Evaluation

Figure 6:
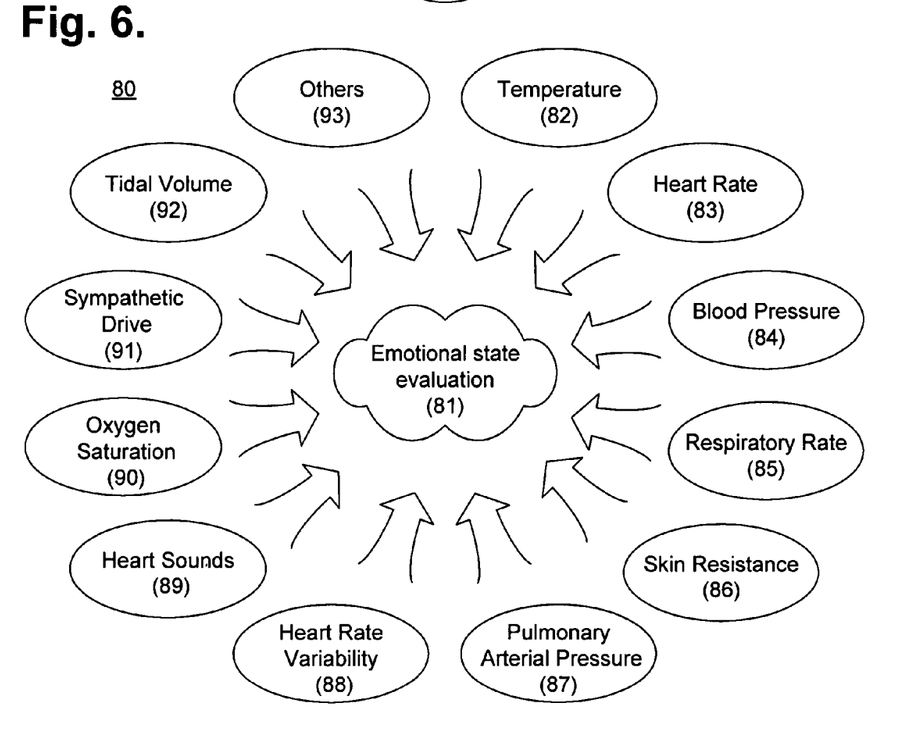
FIG. 6 is a data flow diagram showing evaluation of emotional state for use with the method of FIG. 5.

Both the qualitative and quantitative assessments are considered in determining patient compliance based on perceived emotional state. FIG. 6 is a data flow diagram showing evaluation of emotional state 80 for use with the method 70 of FIG. 5. Importantly, the observed non-normative or unexpected physiometry signals a perceived change in the patient's emotional state, but is not conclusive of psychologically inferable outcomes, such as deceit, anger, evasiveness, or other cognitive mental state. Nevertheless, the emotional state can be an indicator of possible emotional imbalance or instability, which warrants further inquiry or follow up.

The qualitative and quantitative data together enable a holistic assessment of whether the patient is in actual compliance with their prescribed course of treatment and is emotionally stable. During evaluation, the patient's physiometric data is used to corroborate the patient's claimed compliance and to identify possible emotional imbalance. The emotional state evaluation (operation 81) identifies non-normative or unexpected physiological responses, which can indicate an area of potential non-compliance or emotional instability. By way of example, the physiometry includes the patient's temperature 82, heart rate 83, blood pressure 84, respiratory rate 85, skin resistance 86, pulmonary arterial pressure 87, heart rate variability 88, heart sounds 89, oxygen saturation 90, sympathetic drive 91, and tidal volume 92. Skin resistance 86, for instance, indicates lower impedance due to increased perspiration. No single type or level of physiometry is determinative of the patient's emotional state and other types of physiometry 93 or non-physiometric data are possible. Other forms of emotional state evaluation are possible.

Post Processing

Figure 7:
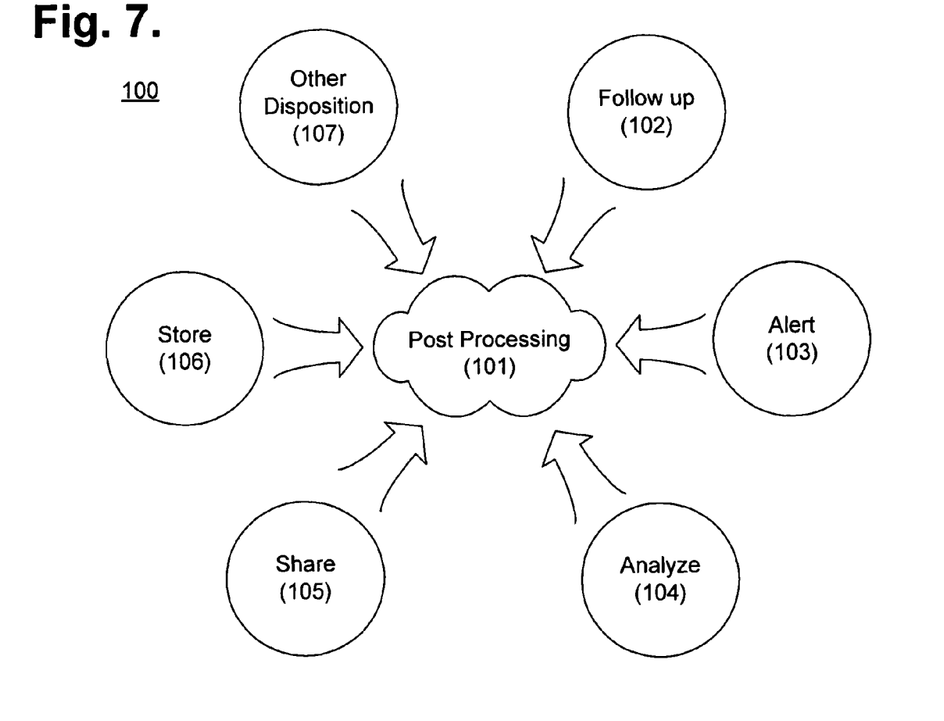
FIG. 7 is a data flow diagram showing post processing of a patient compliance evaluation for use with the method of FIG. 5.

Results of the emotional state evaluation can be used to improve patient care giving through post processing. FIG. 7 is a data flow diagram showing post processing of a patient compliance evaluation 100 for use with the method 70 of FIG. 5. The post processing can be applied to the patient under evaluation; patient peer group, that is, a patient population sharing a chronic disorder or other common set of characteristics; or patient population in general.

Post processing (operation 101) can commence following an evaluation of each compliance response, after the evaluation at the end of a series or section of questions pertained to a specific compliance factor, or upon the completion of evaluation at the close of a compliance checking session. Post processing can include follow up with the patient or custodians charged with day-to-day patient care (operation 102). Post processing can also include generating an alert to the physician or caregiver responsible for the patient (operation 103). The alert can include any factors or indications of perceived non-compliance. Post processing can also include analyzing the patient's emotional state further (operation 104), such as by the server 17 (shown in FIG. 1) or other system; sharing the evaluation (operation 105); or storing the evaluation (operation 106), such as in combination with other patient data. Still further post processing dispositions (operation 107) are possible.

Normative State Determination

Figure 8:
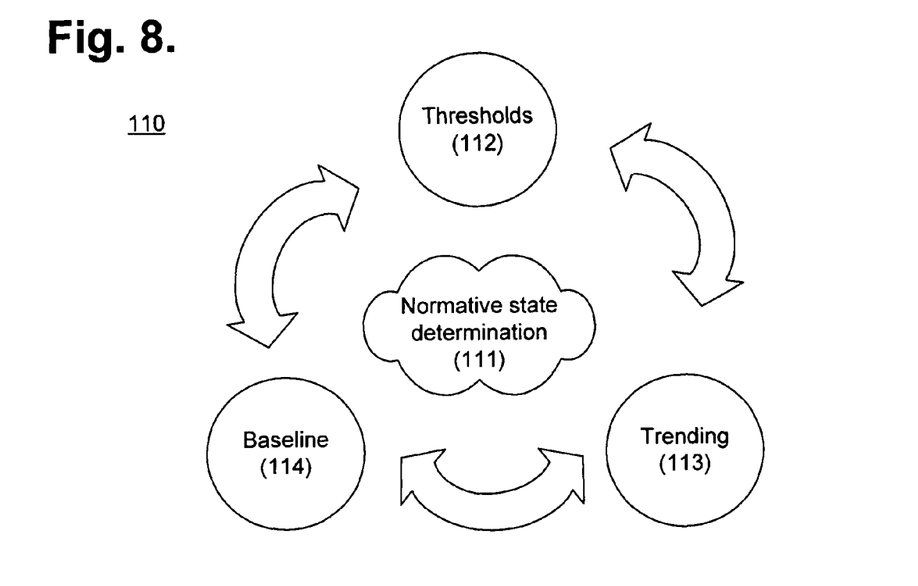
FIG. 8 is a data flow diagram showing normative state determination.

The physiological data recorded during compliance evaluation is evaluated to identify non-normative or unexpected physiological responses. FIG. 8 is a data flow diagram showing normative state determination 110. The "normative" state can be defined on a patient specific, patient peer group, or general patient population basis.

A normative state determination (operation 111) establishes a criteria against which the physiometry recorded during compliance checking is compared or evaluated. Several approaches are possible. For instance, thresholds 112 can be defined to set absolute or relative values or ranges of expected physiometry. During evaluation, those physiometric measures that exceed the thresholds are flagged as possible indications of emotional imbalance. Trending data 113 can also be used to establish a normalized response profile for a particular patient or patient population. Marked departures from the reference physiometry can indicate potential emotional imbalance. Similarly, baseline data 114 could be collected at the outset of compliance checking to establish a starting point for subsequent evaluations. The patient can be tested against a standardized battery of reference questions that determine a set of baseline physiometric data. Other approaches to normative state determination are possible.

Functional Modules

Figure 9:
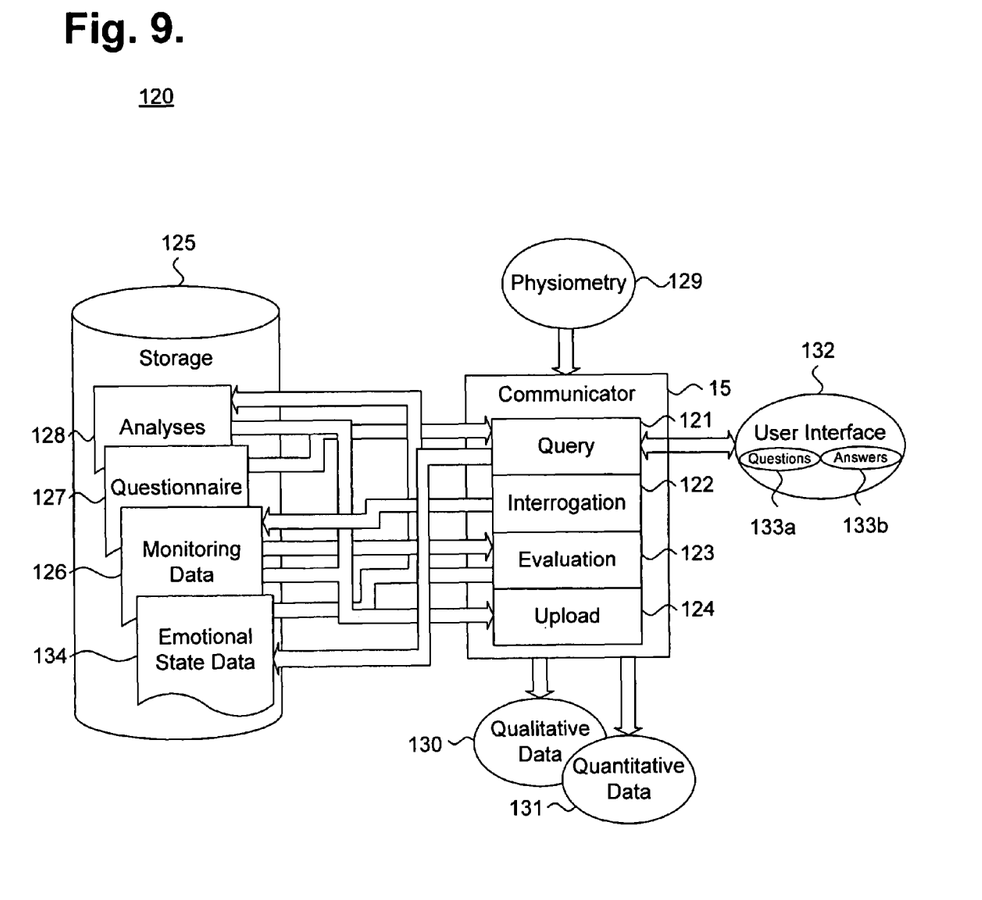
FIG. 9 is a block diagram showing functional modules executed by the communicator of FIG. 2.

Patient compliance can be remotely evaluated through a dedicated patient-operable device, such as a communicator. FIG. 9 is a block diagram showing functional modules 120 executed by the communicator 15 of FIG. 2. Communicators and the broader category of remote medical device interrogators generally are equipped with both a user interface and the capability to collect physiometry contemporaneous to patient questioning.

The communicator 15 includes query 121, interrogation 122, evaluation 123, and upload 124 modules, plus a storage device 125. The query module 121 applies a questionnaire 127 obtained from the storage device 125 through the user interface 132. The questionnaire 127 includes questions 133a that solicit answers 133b from the patient. The query module 121 also receives physiometry 129 measured through sensors 13 (shown in FIG. 1) and, in further embodiment, through patient medical devices 12 (also shown in FIG. 1), contemporaneous to the application of the questionnaire 127. The physiometry 129 and answers 133b are corroborated and stored as emotional state data 134 in the storage device 125. The evaluation module 123 evaluates patient compliance, emotional stability, or both, by analyzing the qualitative data 130 and quantitative data 131 to form analyses 128 of indicated emotional state, which are maintained in the storage device 125. Finally, the upload module 124 periodically interfaces to a server 17, or other centralized repository, to the analyses 128 for further review, evaluation, or other post-processing disposition. Other functional modules are possible.

In a further embodiment, where the patient is also a recipient of a medical device, the interrogation module 122 interrogates the medical device to retrieve recorded monitoring physiometric data and, if applicable, to apply programming to the device. The interrogation module 122 stores the monitoring physiometric data as monitoring data 126 in the storage device 125, which the upload module 124 periodically sends to the server 17, or other centralized repository.

Finally, although described with reference to a self-contained communicator-type device implemented in a dedicated form factor, the functionality provided can also be performed through other types of general purpose programmable devices, such as a personal computer, cellular telephone, or other network-capable device.

While the invention has been particularly shown and described as referenced to the embodiments thereof, those skilled in the art will understand that the foregoing and other changes in form and detail may be made therein without departing from the spirit and scope of the invention.

What is claimed is:

1. A system for remotely evaluating compliance of a patient to a prescribed course of treatment, comprising:
   an implantable medical device (IMD) implanted in the patient, the IMD comprising one or more sensors;
   a query module configured to check compliance to the course of treatment of a patient under remote management on a periodic and regular basis,
   the query module comprising a communicator configured to provide an interactive user interface for performing a qualitative inquiry of patient compliance and emotional state,
   the communicator further configured to receive responses to the qualitative inquiry;
   wherein the one or more sensors are configured to remotely monitor health related physiometry of the patient contemporaneously with the qualitative inquiry;
   a data storage device configured to store physiometry and the responses to the qualitative inquiry; and
   an evaluation module configured to evaluate patient compliance based upon a comparison of the physiometry to baseline physiometric data and configured to assess contemporaneously received responses to the qualitative inquiry to determine an emotional state and to corroborate patient compliance with the determined emotional state,
   wherein the evaluation module is further configured to identify emotional imbalance based upon the comparison of the physiometry to baseline physiometric data and the assessment of the contemporaneously received responses to the qualitative inquiry, and
   wherein the evaluation module is further configured to output information regarding at least one of corroborating compliance, identifying an emotional imbalance, or a combination thereof, which is related to patient compliance toward the prescribed course of treatment.

2. A system according to claim 1, wherein the data storage device further comprises: stored factors bearing on patient compliance selected from the group consisting of medication, dietary restrictions, lifestyle modifications; and combinations thereof.

3. A system according to claim 1, wherein the evaluation module further comprises:
   a relative scale for determining emotional stability along a continuum or discrete set of emotional levels.

4. A system according to claim 1, wherein the interactive user interface comprises one or more of:
   a strictly formatted qualitative inquiry, comprising questions and answers;
   an intermediately formatted qualitative inquiry, comprising one or more of visual analog scales, five factor wellness scales, comfort scales, pain scales, stress scales, and spiritual wellness scales;
   a loosely formatted qualitative inquiry, comprising one or more of written wellness journals, spoken wellness journals, present-time day logs, and time-to-time day logs; or a combination thereof.

5. A system according to claim 1, wherein the evaluation module performs the evaluation following one or more of each response to the qualitative inquiry, at an end of a section of the qualitative inquiry, and upon completion of the qualitative inquiry.

6. A system according to claim 1, wherein the evaluation module dynamically modifies at least one of a nature, ordering, and directness of the evaluation.

7. A system according to claim 6, wherein the dynamic modification is based upon a perceived departure from normative or expected values.

8. A system according to claim 7, wherein the evaluation module further comprises:
one or more of stored thresholds, trending, and baseline data to define the normative or expected values.

9. A system according to claim 1, wherein the physiometry is selected from the group consisting of temperature, heart rate, blood pressure, respiratory rate, skin resistance, pulmonary arterial pressure, heart rate variability, heart sounds, oxygen saturation, sympathetic drive, tidal volume, and combinations thereof.

10. A system according to claim 1, further comprising:
a post processing module to post process the evaluation on a patient specific, patient peer group, or general patient population basis.

11. A system according to claim 10, wherein the post processing comprises one or more of following up, alerting, analyzing, sharing, and storing the evaluation.

12. A system according to claim 1, further comprising:
a compliance checking device comprising at least one of a self-contained communicator-type device and a general purpose programmable device; and
a physiometry monitor comprising at least one of an internal sensor and an external sensor.

13. A method for remotely evaluating compliance of a patient to a prescribed course of treatment, comprising:
checking compliance to the course of treatment on a periodic and regular basis through qualitative inquiry of a patient under remote management, and receiving responses to the qualitative inquiry;
remotely monitoring health related physiometry of the patient contemporaneously with the qualitative inquiry using an implantable medical device (IMD) implanted in the patient;
evaluating patient compliance status based upon a comparison of the physiometry to baseline physiometric data and assessing contemporaneously received responses to the qualitative inquiry to determine an emotional state and to corroborate patient compliance with the determined emotional state;
determining whether emotional imbalance exists based upon the comparison of the physiometry to baseline physiometric data and to the assessment of the contemporaneously received responses to the qualitative inquiry; and
outputting information regarding at least one of corroborating compliance, identifying an emotional imbalance, or a combination thereof, which is related to patient compliance toward the prescribed course of treatment.

14. A method according to claim 13, further comprising:
setting factors bearing on patient compliance selected from the group consisting of medication, dietary restrictions, lifestyle modifications, and a combination thereof.

15. A method according to claim 13, further comprising:
determining emotional stability using a relative scale along a continuum or discrete set of emotional levels.

16. A method according to claim 13, further comprising one or more of:
formatting the qualitative inquiry in a strict format, comprising questions and answers;
formatting the qualitative inquiry in an intermediate format, comprising one or more of visual analog scales, five factor wellness scales, comfort scales, pain scales, stress scales, and spiritual wellness scales; and
formatting the qualitative inquiry in a loose format, comprising one or more of written wellness journals, spoken wellness journals, present-time day logs, and time-to-time day logs.

17. A method according to claim 13, further comprising one or more of:
performing the evaluation following each response to the qualitative inquiry;
performing the evaluation at an end of a section of the qualitative inquiry; and
performing the evaluation upon completion of the qualitative inquiry.

18. A method according to claim 13, further comprising:
dynamically modifying at least one of a nature, ordering, and directness of the evaluation.

19. A method according to claim 18, further comprising:
basing the dynamic modification upon a perceived departure from normative or expected values.

20. A method according to claim 19, further comprising:
defining the normative or expected values as one or more of thresholds, trending, and baseline data.

21. A method according to claim 13, wherein the physiometry is selected from the group consisting of temperature, heart rate, blood pressure, respiratory rate, skin resistance, pulmonary arterial pressure, heart rate variability, heart sounds, oxygen saturation, sympathetic drive, tidal volume, and combinations thereof.

22. A method according to claim 13, further comprising:
post processing the evaluation on a patient specific, patient peer group, or general patient population basis.

23. A method according to claim 22, wherein the post processing comprises one or more of following up, alerting, analyzing, sharing, and storing the evaluation.

24. A method according to claim 13, further comprising:
compliance checking the patient using at least one of a self-contained communicator-type device and a general purpose programmable device; and
physiometry monitoring using at least one of an internal sensor and an external sensor.

25. A non-transitory computer-readable storage medium storing instructions that, when executed by a computer, cause the computer to perform the method according to claim 13.

26. An apparatus for remotely evaluating compliance of a patient to a prescribed course of treatment, comprising:
means for checking compliance to the course of treatment on a periodic and regular basis through qualitative inquiry of a patient under remote management and receiving responses to the qualitative inquiry;
means for remotely monitoring health related physiometry of the patient contemporaneously with the qualitative inquiry using an implantable medical device (IMD) implanted in the patient; and
means for evaluating patient compliance, comprising means for determining an emotional state and corroborating compliance with the determined emotional state based upon a comparison of the physiometry to baseline physiometric data and an assessment of the contemporaneously received responses to the qualitative inquiry, wherein the means for evaluating further comprises at least one means for identifying an emotional imbalance based upon a comparison of the physiometry to baseline physiometric data and to the assessment of the contemporaneously received responses to the qualitative inquiry, and wherein the means for evaluating further comprises means to output information regarding at least one of corroborating compliance, identifying an emotional imbalance, or a combination thereof, which is related to patient compliance toward the prescribed course of treatment.

* * * * *